United States Patent [19]

Grill et al.

[11] Patent Number: 4,582,857
[45] Date of Patent: Apr. 15, 1986

[54] NOVEL P-OXYBENZOIC ACID DERIVATIVES, PROCESSES FOR THEIR PRODUCTION AND THEIR USE AS DRUGS

[75] Inventors: Helmut Grill, Vaterstetten; Friedemann Reiter, Putzbrunn; Roland Löser, Feldafing; Michael Schliack, Munich; Klaus Seibel, Gräfelfing, all of Fed. Rep. of Germany

[73] Assignee: Klinge Pharma GmbH, Munich, Fed. Rep. of Germany

[21] Appl. No.: 632,650

[22] Filed: Jul. 20, 1984

[30] Foreign Application Priority Data

Jul. 20, 1983 [DE] Fed. Rep. of Germany ....... 3326164

[51] Int. Cl.[4] .................. C07C 103/29; A61K 31/195
[52] U.S. Cl. .................................... 514/563; 514/568; 562/463; 562/444; 562/475
[58] Field of Search ............... 424/317, 319; 562/475, 562/463, 444, 445; 514/561, 568, 563

[56] References Cited

U.S. PATENT DOCUMENTS

| | | | |
|---|---|---|---|
| 3,586,713 | 6/1971 | Bure-Hoi et al. | 562/444 |
| 3,968,143 | 7/1976 | Schacht et al. | 424/317 |
| 4,067,892 | 1/1978 | Thorne et al. | 562/463 |
| 4,073,935 | 2/1978 | Grill et al. | 424/314 |
| 4,151,302 | 4/1979 | Gante et al. | 424/317 |
| 4,154,850 | 5/1979 | Morgan et al. | 424/317 |
| 4,189,594 | 2/1980 | Grill et al. | 424/317 |
| 4,277,497 | 7/1981 | Fromantin | 424/317 |

OTHER PUBLICATIONS

Morris et al, "Organic Chemistry", pp. 1112–1113 (1966).
Fieser et al, "Reagents for Organic Synthesis", pp. 303–309 (1968).

Primary Examiner—James H. Reamer
Attorney, Agent, or Firm—Burns, Doane, Swecker & Mathis

[57] ABSTRACT

P-oxybenzoic acid derivatives of formula (1)

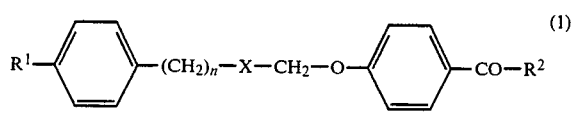

wherein
$R^1$ is hydrogen, or straight or branched alkyl of one to four carbon atoms;
n is 1 or 2;
X is

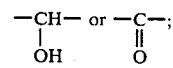

and
$R^2$ is —OH or —NHCH$_2$COOH; and non-toxic pharmaceutically acceptable salts thereof.

The compounds exhibit a hypolipemic effect. They may be prepared by methods known in themselves from the corresponding ester or acid halide compounds, wherein optionally the secondary alcohol group may be oxidized to a keto group.

8 Claims, No Drawings

NOVEL P-OXYBENZOIC ACID DERIVATIVES, PROCESSES FOR THEIR PRODUCTION AND THEIR USE AS DRUGS

BACKGROUND OF THE INVENTION

In the treatment by medication of hyperlipidemia mainly aryloxyisoalkanoic acids are used, the best known active ingredient being ethyl 2-(4'-chlorophenoxy)-2-methylpropionate (clofibrate). It has been found, however, that clofibrate has an unsatisfactory therapeutic effect.

It is further known that certain benzoic acids etherized in the para position also have hypolipemic properties. Benzoic acid derivatives derived from ethers of glycerine (West German Patentschrift No. 24 60 689) and 1,3-dihydroxyacetone (West German Offenlegungsschrift No. 27 35 856) are known.

SUMMARY OF THE INVENTION

The present invention comprises p-oxybenzoic acid derivatives of formula (1)

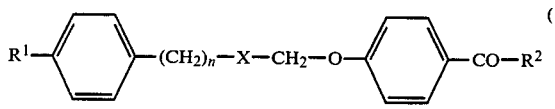

wherein
$R^1$ is hydrogen, or straight or branched alkyl of one to four carbon atoms;
n is 1 or 2;
x is

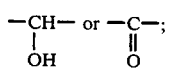

and
$R^2$ is —OH or —NHCH$_2$COOH; or
non-toxic, pharmaceutically acceptable salts thereof.

DETAILED DESCRIPTION OF THE INVENTION

It has now been surprisingly found that benzoic acid derivatives of formula (1) above also have hypolipemic effects. As the known, hypolipemically effective substances are ether derivatives of glycerin or ether compounds of dioxyacetone (an oxidation product of glycerin), one would conclude that these substances are effective as the result of their glycerine structure, i.e., as relatives of the natural glycerides. It could not have been anticipated therefore that ether compounds of p-oxybenzoic acid or its acid amides substituted in a certain manner with divalent alcohol derivatives, i.e., derivatives of glycol or its oxidation products, would also have hypolipemic effects.

Equivalent to the compounds of formula (1) for the purposes of the present invention are the non-toxic, pharmaceutically acceptable salts thereof. Preparation of the salts according to formula (1) is accomplished by allowing the corresponding acids, preferably in aqueous-alcoholic medium, to react with bases of the alkali or alkaline earth series, aluminum bases, as well as ammonia or other therapeutically acceptable amines, by known methods.

The preparation of these new, hypolipemically active compounds may be effected in a manner known in itself, in which according to the invention the following processes are used:

(a) compounds of the general formula (2)

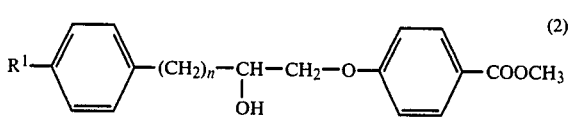

wherein $R^1$ and n are as defined above, are saponified with alkali, the carboxyl group liberated by the addition of a mineral acid, and after crystallization, optionally converted to the corresponding salts by bases;

(b) compounds of the general formula (3)

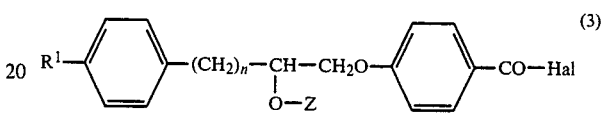

wherein $R^1$ and n are as defined above, Z is a protective group (for example, acetyl), and Hal represents a halogen atom (preferably chlorine) are reacted with sodium glycinate in a manner known in itself, whereupon the protective group is cleaved by alkali, the carboxyl groups released by the addition of a mineral acid, and after crystallization, optionally converted to the corresponding salts by bases;

(c) compounds of the general formula (4)

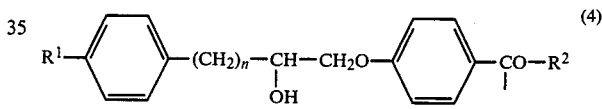

wherein $R^1$, n and $R^2$ are as defined above are oxidized with dimethylsulfoxide, the oxidation product crystallized, and optionally converted by bases to the corresponding salts.

The starting materials needed for the synthesis of the compounds according to the invention may be prepared for example by the following processes:

By the reaction of epichlorohydrin with Grignard compounds of the general formula (5)

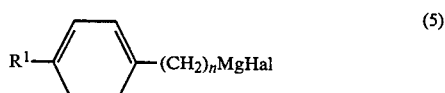

wherein $R^1$ is as defined above, n may be 0 or 1, and Hal represents a suitable halogen atom, compounds of the general formula (6) are obtained,

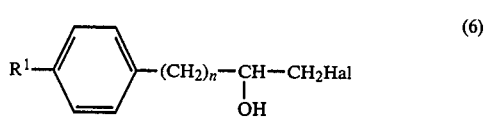

wherein n is 1 or 2, and which in the presence of alkali alcoholates convert to epoxides of the general formula (7).

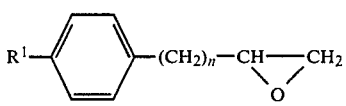

Compounds of the general formula (7) react with 4-hydroxybenzoic acid esters, for example with methyl 4-hydroxybenzoate, in the presence of alkali to form compounds of the general formula (8)

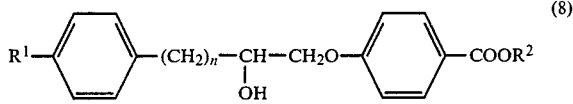

wherein $R^1$ and n are as defined above for formula (1), and $R^2$ is a suitable alkyl residue.

By means of alkaline saponification and subsequent acidification with a mineral acid, compounds according to the invention of the general formula (9) are obtained.

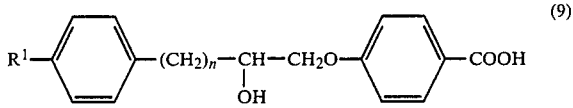

Conversion with acetyl chloride yields compounds of the general formula (10)

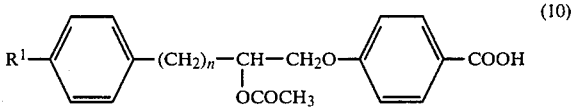

which may be converted by thionyl chloride into acid chlorides of the general formula (11)

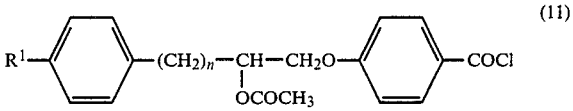

After reaction with sodium glycinate and subsequent alkaline saponification, the compounds according to the invention of general formula (12) are released by acidification with a mineral acid

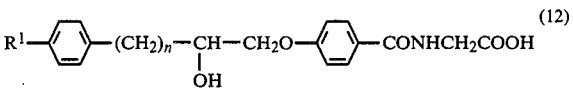

wherein $R^1$ and n are as defined in Formula (1). By selective oxidation with dimethylsulfoxide, compounds of the general formulas (9) and (12) are converted into ketones of the general formula (13),

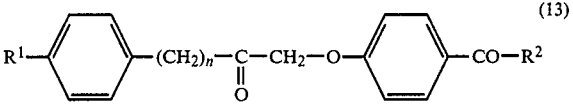

wherein $R^1$, n and $R^2$ are as defined in Formula (1).

The present invention also concerns compositions comprising a compound of the general formula (1) or a non-toxic, pharmaceutically acceptable salt thereof as active ingredient and a non-toxic, pharmaceutically acceptable carrier therefor, e.g., one or more of the conventional pharmaceutical carriers and adjuvants. The active ingredient is present in an effective amount (a hypolipiemically effective amount).

The claimed compounds are preferably administered orally. Usually the oral dose amounts to 1.5 and 70.0 mg/kg body weight, preferably 4 to 30 mg/kg body weight, for a mammal weighing approximately 70 kg. Nevertheless, it can under certain circumstances be necessary to deviate from the above doses, depending upon the individual behavior with respect to the medicament or the kind of formulation and the point of time or the interval at which the administration takes place. Thus it can be sufficient in some cases to manage with less than the above minimum amount, while in other cases the above-mentioned upper limit must be exceeded. In the case of application of larger amounts, it can be advisable to divide these into several individual doses through the day. The active ingredient can be made up in conventional form for oral administration e.g., in capsules, as tablets or as dragees. The release of the claimed compounds can be accelerated or delayed according to pharmaceutical adaptation.

As pharmaceutical carrier substances, conventional materials may be used, such as lactose, saccharose, mannite, potato or corn starch, cellulose derivatives or gelatin, possibly with the addition of lubricants, such as magnesium or calcium stearate and polyethylene glycols.

Preferred forms of administration are two-part capsules of hard gelatin and closed soft gelatin capsules. The push-together capsules contain the active ingredient preferably as a granulate e.g., mixed with fillers such as lactose, saccharose, mannite, starches such as e.g., potato starch or corn starch, microcrystalline cellulose, cellulose derivatives, gelatin or highly dispersed silicates, and optionally a slight amount of lubricants. In soft gelatin capsules the active ingredient is dissolved or suspended in suitable fluids, e.g., in plant oils or in fluid polyethylene glycols.

To obtain a more complete understanding of the present invention, the following examples are set forth. However, it should be understood that the invention is not limited to the specific details set forth in the following examples.

EXAMPLE 1

4-[4-(4'-tert.-butylphenyl)-2-hydroxybutoxy]benzoic acid (a) 4-(4'-tert.-butylphenyl)-1,2-epoxybutane A Grignard solution freshly prepared from 12.15 g (0.50 gram atom) magnesium chips and 91.7 g (0.50 mole) 4-tert.-butylbenzyl chloride in 550 ml dry ether is dripped with agitation into a precooled solution of 92.5 g (1.00 mole) epichlorohydrin in 165 ml dry ether, so that the temperature does not exceed $-40°$ C. After addition is complete, the cooling bath is removed, the solution is allowed to stand for several hours at room temperature, and then hydrolyzed with ice water and dilute hydrochloric acid. The ether phase is separated, washed with water and dried over sodium sulfate. After the ether has been drawn off, the bath temperature is raised to 80° C. and the volatile components carefully removed at 0.1 mbar. The residue is taken up in 270 ml methanol and a freshly prepared solution of 6.90 g (0.30 g atom) sodium in 200 ml methanol added at room temperature. After three hours the sodium chloride precipitated is separated, the filtrate concentrated in vacuum, the residue taken up in ether and washed with water. After drying over sodium sulfate the solvent is removed and the oily residue distilled in vacuum. A colorless liquid with a boiling point of 79°–81° C./0.1 mbar is obtained.

Yield: 40.0 g (39%).

| $^1$H—NMR spectrum (CDCl$_3$)*: | 1.33 s (9) | (C$\underline{H}_3$)$_3$C |
|---|---|---|
| | 1.53 to 2.07 m (2) | ArCH$_2$C$\underline{H}_2$ |
| | 2.23 to 3.13 m (5) | ArC$\underline{H}_2$C$\underline{H}_2$ |
| | | C$\underline{H}$——C$\underline{H}_2$ \ / O |
| | 7.17 (center) m (4) | aromatic |

*Taken at 60 MHZ
The chemical shifts are given in ppm against TMS (δ = 0.0), the relative intensities being shown in parentheses.
s = singulet, d = doublet, t = triplet, q = quartet, m = multiplet (b) Methyl-4-[4-(4'-tert.-butylphenyl)-2-hydroxybutoxy]-benzoate 40.0 g (0.196 mole) 4-(4'-tert-butylphenyl)-1,2-epoxybutane are heated with 31.7 g (0.214 mole) methyl-4-hydroxybenzoate and 1.38 g potassium hydroxide in 170 ml methanol for 60 hours with reflux. Subsequently, the solution is concentrated in vacuum, the residue taken up in ether, shaken with 1N sodium hydroxide and water. After drying over sodium sulfate, the ether is removed in vacuum and the oily residue crystallized from diisopropylether. Colorless crystals with a melting point of 77°–78° C. are obtained.

Yield: 43.3 g (62%).

| $^1$H—NMR-spectrum (CDCl$_3$): | 1.33 s (9) | (C$\underline{H}_3$)$_3$C |
|---|---|---|
| | 1.63 to 2.23 m (2) | ArCH$_2$C$\underline{H}_2$ |
| | 2.47 d (1) | O$\underline{H}$ |
| | 2.60 to 3.07 m (2) | ArC$\underline{H}_2$CH$_2$ |
| | 3.77 to 4.33 m and 3.90 s (6) | C$\underline{H}$—C$\underline{H}_2$O C$\underline{H}_3$O |
| | 6.73 to 8.23 m (8) | aromatic | c. Preparation of 4-[4-(4'-tert.-butylphenyl)-2-hydroxybutoxy]benzoic acid according to the invention 35.6 g (0.10 mole) methyl-4-[4-[4'-tert.-butylphenyl]-2-hydroxybutoxy]benzoate are heated in a solution of 18.0 g (0.32 mole) potassium hydroxide in 125 ml ethanol for 1.5 hours with reflux. Subsequently, the solvent is removed in vacuum, the residue taken up in water, extracted with ether and the aqueous phase acidified with concentrated hydrochloric acid. The product precipitated is taken up in ethyl acetate and the organic phase washed with water. After drying over sodium sulfate the solvent is removed in vacuum and the residue crystallized twice from acetonitrile. Colorless crystals with a melting point of 142°–143° C. are obtained.

Yield: 23.6 g (69%).
C$_{21}$H$_{26}$O$_4$: (342.4).

Molecular weight: 342 determined by electron impact ionization (70 eV) mass spectrometry.

IR spectrum (KBr): ν(OH) 3600 to 2500 cm$^{-1}$; ν(C=O) 1680 cm$^{-1}$.

| $^1$H—NMR spectrum (CDCl$_3$): | 1.30 s (9) | (C$\underline{H}_3$)$_3$C |
|---|---|---|
| | 1.73 to 2.17 m (2) | ArCH$_2$C$\underline{H}_2$ |
| | 2.63 to 3.03 m (2) | ArC$\underline{H}_2$CH$_2$ |
| | 3.80 to 4.27 m (3) | C$\underline{H}$C$\underline{H}_2$O |
| | 6.67 to 8.20 m (10) | aromatic O$\underline{H}$ COO$\underline{H}$ |

EXAMPLE 2

4-[3-(4'-ethylphenyl)-2-hydroxypropoxy]benzoic acid (a) 3-(4'-ethylphenyl)-1,2-epoxypropane A Grignard solution freshly prepared from 12.15 g (0.50 g atom) magnesium chips and 92.5 g (0.50 mole) 1-bromo-4-ethylbenzene in 400 ml dry ether is dripped with agitation into a precooled solution of 92.5 g (1.00 mole) of epichlorohydrin in 100 ml of dry ether, so that the temperature does not exceed −40° C. After addition is complete, the solution is heated slowly to 20° C. and is hydrolyzed after another three hours by the addition of ice water and dilute hydrochloric acid. The ether phase is separated, washed twice with water and dried over sodium sulfate. Following the removal of the ether, the bath temperature is raised to 70° C. and the volatile components carefully removed at 0.1 mbar. The residue is taken up in 185 ml of methanol and a freshly prepared solution of 6.90 g (0.30 g atom) sodium in methanol added at room temperature. After three hours the sodium chloride precipitate is separated, the filtrate concentrated in vacuum and the yellow, oily residue used without purification for further conversion.

Raw yield: 49.3 g (60%).

| $^1$H—NMR spectrum (CDCl$_3$): | 1.20 t (3) | |
|---|---|---|
| | 2.37 to 3.30 m (7) | 2 ArC$\underline{H}_2$, C$\underline{H}$——C$\underline{H}_2$ \ / O |
| | 7.20 s (4) | aromatic |

(b) Methyl-4-[3-(4'-ethylphenyl)-2-hydroxypropoxy]benzoate 49.0 g (0.30 mole) raw 3-(4'-ethylphenyl)-1,2-epoxypropane are heated with 48.6 g (0.32 mole) methyl-4-hydroxybenzoate and 0.94 g potassium hydroxide in 130 ml methanol for 47 hours under reflux, while another 0.40 g potassium hydroxide is added after 20 and 40 hours. The cooled solution is poured into water, shaken twice with dichloromethane and the combined organic phases washed with water. After drying over sodium sulfate, the solvent is removed by vacuum and the solid residue crystallized from ethanol. Colorless crystals with a melting point of 113°–114° C. are obtained.

Yield: 49.7 g (53%).

| $^1$H—NMR spectrum (CDCl$_3$): | 1.20 t (3) | CH$_2$C$\underline{H}_3$ |
|---|---|---|
| | 2.40 to 3.03 m (5) | 2ArC$\underline{H}_2$ O$\underline{H}$ |
| | 3.77 to 4.40 m and 3.87 s (6) | C$\underline{H}$C$\underline{H}_2$ |

-continued

| | |
|---|---|
| 6.77 to 8.13 m and 7.13 s (8) | OC$\underline{H}_3$ aromatic |

(c) Preparation according to the invention of 4-[3-(4'-ethylphenyl)-2-hydroxypropoxy]benzoic acid 31.4 g (0.10 mole) methyl-4-[3-(4'-ethylphenyl)-2-hydroxypropoxy]benzoate are heated with a solution of 16.0 g (0.29 mole) potassium hydroxide in 170 ml ethanol for three hours with agitation and under reflux, whereby the potassium salt of the final product is precipitated. Following cooling, the suspension is poured into water and the clear solution obtained acidified with concentrated hydrochloric acid. The precipitated end product is suctioned off, washed several times with water and crystallized from ethyl acetate/ethanol. Colorless crystals with a melting point of 168°–170° C. are obtained.

Yield 23.6 (79%).

$C_{18}H_{20}O_4$: (300.3).

Molecular weight: 300 (determined by mass spectrometry).

IR spectrum (KBr): $\nu$(O—H) 3600 to 2400 cm$^{-1}$; $\nu$(C=O) 1680 cm$^{-1}$.

| $^1$H—NMR spectrum (d$_6$-acetone/d$_6$-DMSO) | |
|---|---|
| 1.17 t (3) | C$\underline{H}_3$ |
| 2.37 to 3.03 m (4) | 2ArC$\underline{H}_2$ |
| 3.90 to 4.30 m (3) | C$\underline{H}$C$\underline{H}_2$O |
| 6.87 to 8.17 m and 7.17 s (8) | aromatic |

In a manner analogous to Examples 1 and 2, further compounds of general formula (9) were prepared and are listed in Table 1 with their melting points. For the sake of completeness, the compounds described in the above examples are listed again in the following table.

TABLE 1

$$R^1-\text{C}_6\text{H}_4-(CH_2)_n-\underset{\underset{OH}{|}}{CH}-CH_2O-\text{C}_6\text{H}_4-COOH \quad (9)$$

| No. | $R^1$ | n | Melting point (°C.)* | Solvent** |
|---|---|---|---|---|
| 1 | H | 1 | 150–152 | (a) |
| 2 | CH$_3$ | 1 | 168–169 | (b) |
| 3 | CH$_3$CH$_2$ | 1 | 168–170 | (c) |
| 4 | (CH$_3$)$_2$CH | 1 | 154–156 | (d) |
| 5 | (CH$_3$)$_3$C | 1 | 189–190 | (a) |
| 6 | H | 2 | 73–76 | (a) |
| 7 | CH$_3$CH$_2$ | 2 | 111–112 | (a) |
| 8 | (CH$_3$)$_3$C | 2 | 142–143 | (a) |

*Melting points were determined by means of a Kofler heated stage microscope and are not corrected.
**Crystals from
(a): acetonitrile
(b): ethyl acetate
(c): ethyl acetate/ethanol
(d): ethyl acetate/acetonitrile.

EXAMPLE 3

N-carboxymethyl-4-[4-(4'-tert.-butylphenyl)-2-hydroxybutoxy]benzamide (a) 4-[4-(4'-tert.-butylphenyl)-2-acetoxybutoxy]benzoic acid 34.2 g (0.10 mole) 4-[4-(4'tert.-butylphenyl)-2-hydroxybutoxy]benzoic acid and 0.30 g (2.2 mmole) anhydrous zinc chloride are dissolved in 240 ml anhydrous acetic acid and mixed with 15.8 ml (0.22 mole) acetyl chloride. After agitation for three hours at room temperature, the reaction solution is poured into ice water. The product precipitated is taken up in ether and washed with water. After drying over sodium sulfate the ether is removed in vacuum, and the colorless crystalline raw product used in further reactions without purification.

Raw yield: 37.4 g (97%).

| $^1$H—NMR spectrum (CDCl$_3$) | |
|---|---|
| 1.30 s (9) | (C$\underline{H}_3$)$_3$C |
| 1.83 to 2.33 m and 2.07 s (5) | ArCH$_2$C$\underline{H}_2$ C$\underline{H}_3$CO |
| 2.50 to 2.93 m (2) | ArC$\underline{H}_2$CH$_2$ |
| 4.10 d (2) | C$\underline{H}_2$O |
| 5.27 m (1) | C$\underline{H}$O |
| 6.77 to 8.27 m (8) | aromatic |
| 10.7 wide s (1) | COO$\underline{H}$ |

(b) Preparation according to the invention of N-carboxymethyl-4-[4-(4'-tert.butylphenyl)-2-hydroxybutoxy]benzamide 37.4 g (0.097 mole) of raw 4-[4-(4'-tert.-butylphenyl)-2-acetoxybutoxy]benzoic acid and 12 ml (0.165 mole) thionyl chloride in 240 ml toluene are heated to reflux for 3.5 hours. Subsequently, the solvent and the excess thionyl chloride are distilled off in vacuum and the oily residue taken up in 250 ml of dry dioxane. This solution is dripped with vigorous agitation at 5° to 7° C. into a solution of 29.5 g (0.39 mole) glycine and 15.6 g (0.39 mole) sodium hydroxide in 350 ml water. After this, agitation is continued for three more hours at room temperature, 30 g sodium hydroxide added and the solution heated for two hours to 50° C. After cooling the mixture is diluted with water and acidified with concentrated hydrochloric acid. The end product precipitated is taken up in ethyl acetate and washed twice with water. After drying over sodium sulfate, the solvent is removed in vacuum and the solid residue crystallized from acetonitrile. Colorless crystals with a melting point of 112°–114° C. are obtained.

Yield: 26.0 g (67%).

$C_{23}H_{29}NO_5$: (399.5).

Molecular weight: 399 (determined by mass spectrometry).

IR spectrum (KBr): $\nu$(O—H), 3600 to 2400 cm$^{-1}$; $\nu$(C=O), 1720 cm$^{-1}$; $\nu$(N—H), 3400 cm$^{-1}$.

| $^1$H—NMR spectrum (d$_6$-acetone/d$_6$-DMSO) | |
|---|---|
| 1.30 s (9) | (C$\underline{H}_3$)$_3$C |
| 1.67 to 2.20 m (2) | ArCH$_2$C$\underline{H}_2$ |
| 2.60 to 3.03 m (2) | ArC$\underline{H}_2$CH$_2$ |
| 3.77 to 4.23 m (5) | C$\underline{H}$C$\underline{H}_2$O, C$\underline{H}_2$N |
| 6.83 to 8.23 m (10) | aromatic, N$\underline{H}$, COO$\underline{H}$ |

In a manner similar to Example 3, further compounds of the general formula (12) were prepared and are listed in Table 2 with their melting points. For the sake of completeness, in Table 2 below the compounds described in Example 3 are again listed.

TABLE 2

$$R^1-\underset{}{\bigcirc}-(CH_2)_n-\underset{OH}{\overset{}{CH}}-CH_2O-\underset{}{\bigcirc}-CONHCH_2COOH \quad (12)$$

| No. | R¹ | n | Melting point (°C.) | Solvent* |
|-----|----|----|---------------------|----------|
| 9 | H | 1 | 152–154 | (a) |
| 10 | CH₃ | 1 | 168–170 | (a) |
| 11 | CH₃CH₂ | 1 | 174–176 | (c) |
| 12 | (CH₃)₃C | 1 | 153–154 | (d) |
| 13 | H | 2 | 98–100 | (b) |
| 14 | CH₃CH₂ | 2 | 117–120 | (d) |
| 15 | (CH₃)₂CH | 2 | 128–130 | (e) |
| 16 | (CH₃)₃C | 2 | 112–114 | (d) |

*Crystals from
(a): ethanol
(b): methanol/water
(c): tetrahydrofuran/ethyl acetate
(d): acetonitrile
(e): ethyl acetate.

EXAMPLE 4

4-[4-(4'-tert.-butylphenyl)-2-oxobutoxy]benzoic acid

To 14.5 ml (0.2 mole) anhydrous dimethylsulfoxide in 180 ml dry dichloromethane under strong agitation at −70° C. are dropwise added 21 ml (0.15 mole) trifluoroacetic acid anhydride in 21 ml dry dichloromethane. The suspension obtained is agitated for another 10 minutes and subsequently mixed slowly with a solution of 34.2 g (0.10 mole) 4-[4-(4'-tert-butylphenyl)-2-hydroxybutoxy]benzoic acid in 73 ml dichloromethane and 18 ml dimethylsulfoxide, so that the temperature does not exceed −50° C. After 30 minutes, 42 ml triethylamine are added carefully and the reaction mixture slowly brought to room temperature by removing the cooling bath. The reaction solution is washed several times with water and after drying over sodium sulfate the solvent removed in vacuum. The residue is crystallized from isopropylacetate/chlorobutane. Colorless crystals with a melting point of 149°–153° C. are obtained.

Yield: 12.2 g (36%).

$C_{21}H_{24}O_4$: (340.4).

Molecular weight: 340 (determined by mass spectrometry).

IR spectrum (KBr): $\nu$(O—H), 3600 to 2500 cm⁻¹; $\nu$(C=O), 1710 cm⁻¹ (ketone), 1675 cm⁻¹ (carboxylic acid).

| ¹H—NMR spectrum (CDCl₃): | |
|---|---|
| 1.30 s (9) | (CH₃)₃C |
| 2.93 s (4) | CH₂CH₂ |
| 4.57 s (2) | CH₂O |
| 6.70 to 8.23 m (8) | aromatic |
| 9.60 wide s (1) | COOH |

EXAMPLE 5

N-carboxymethyl-4-[3-(4'-ethylphenyl)-2-oxopropoxy]benzamide 35.7 g (0.10 mole) N-carboxymethyl-4-[3-(4'-ethylphenyl)-2-hydroxypropoxy]benzamide and 63 ml (0.45 mole) triethylamine in 100 ml dry dimethylsulfoxide are mixed in portions with 48.0 g (0.30 mole) of pyridine-sulfur trioxide complex with ice cooling and agitation. The clear solution is allowed to stand for 6 hours at room temperature, ice water poured in and the solution acidified with concentrated hydrochloride acid. The oil precipitated is taken up in ethyl acetate, the solution washed with water and dried over sodium sulfate. The solvent is removed by vacuum and the residue crystallized from ethyl acetate/acetonitrile. Colorless crystals with a melting point of 142°–145° C. are obtained.

Yield: 17.0 g (48%).

$C_{20}H_{21}NO_5$: (355.3).

Molecular weight: 355 (determined by mass spectrometry).

IR spectrum (KBr): $\nu$(O—H), 3600 to 2800 cm⁻¹; $\nu$(N—H), 3300 cm⁻¹; $\nu$(C=O), 1730 cm⁻¹.

| ¹H—NMR spectrum (d₆-acetone): | |
|---|---|
| 1.23 t (3) | CH₃CH₂ |
| 2.63 q (2) | CH₃CH₂ |
| 3.93 s (2) | ArCH₂CO |
| 4.13 d (2) | CH₂N |
| 4.97 s (2) | CH₂O |
| 6.80 to 8.20 m and 7.20 s (9) | aromatic, NH |

In a manner similar to Examples 4 and 5, further compounds of the general formula (13) were prepared and are listed in Table 3 with their melting points. For the sake of completeness, Table 3 again lists the compounds described in Examples 4 and 5.

TABLE 3

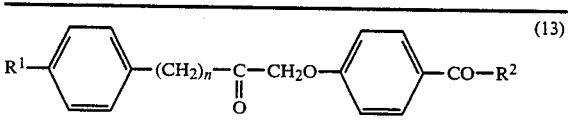

(13)

| No. | R¹ | n | R² | Melting point (°C.) | Solvent* |
|-----|----|----|----|---------------------|----------|
| 17 | H | 1 | OH | 176–180 | (a) |
| 18 | CH₃ | 1 | OH | 182–184 | (d) |
| 19 | CH₃CH₂ | 1 | OH | 177–179 | (e) |
| 20 | (CH₃)₃C | 1 | OH | 163–164 | (b) |
| 21 | H | 2 | OH | 158 (decomp.) | (c) |
| 22 | (CH₃)₂CH | 2 | OH | 160–163 | (b) |
| 23 | (CH₃)₃C | 2 | OH | 149–153 | (i) |
| 24 | H | 1 | NHCH₂COOH | 140–142 | (b) |
| 25 | CH₃ | 1 | NHCH₂COOH | 156–158 | (e) |
| 26 | CH₃CH₂ | 1 | NHCH₂COOH | 142–145 | (f) |
| 27 | (CH₃)₃C | 1 | NHCH₂COOH | 69–73 | (h) |
| 28 | H | 2 | NHCH₂COOH | 139–140 | (b) |
| 29 | (CH₃)₂CH | 2 | NHCH₂COOH | 133–134 | (g) |

*Crystals from
(a): acetonitrile/ethanol
(b): acetonitrile
(c): isopropanol
(d): tetrahydrofuran/ethyl acetate
(e): ethanol/ethyl acetate
(f): acetonitrile/ethyl acetate
(g): ethyl acetate
(h): chlorobutane
(i): chlorobutane/isopropyl acetate

EXAMPLE 6

Medications containing N-carboxymethyl-4-(2-hydroxy-4-phenylbutoxy)benzamide 100 g N-carboxymethyl-4-(2-hydroxy-4-phenylbutoxy)benzamide are mixed well with 16 g corn starch and 6 g highly dispersed silicon dioxide, then wetted with a solution of 2 g stearic acid, 6 g acetyl cellulose and 6 g stearin in 70 ml isopropanol and granulated. The dry granulate is passed through a sieve and pressed after mixing with 16 g corn starch, 16 g talcum powder and 2 g magnesium stearate into 1000 dragee cores. After coating with a syrup of 2 g lacca, 7.5 g gum arabic, 0.15 g colorant, 2 g colloidal silicon dioxide, 25 g talcum and 53.35 g saccharose, pills weighing 260 mg were obtained after drying, each containing 100 mg of active ingredients.

EXAMPLE 7

Medications containing 4-[4-(4'-tert.-butylphenyl)-2-oxobutoxy]benzoic acid 250 g 4-[4-(4'-tert.-butylphenyl)-2-oxobutoxy[benzoic acid are mixed with 250 g polyethylene glycol and filled into 1000 soft gelatin capsules, each containing 250 mg of the active ingredient.

The superiority of the compounds claimed with respect to the clofibrate used for a long period of time in therapy may be demonstrated unambiguously by means of their lipid reducing effect.

The lipid lowering effect was tested on groups of 10 normally fed, normolipemic, male Wistar rats weighing 200 to 220 g.

The test compounds were taken up in an aqueous solution of 0.25% agar and 0.85% sodium chloride and administered orally. Following the application of 4×100 mg/kg over a period of four days the animals were bled by cardiac puncture after having been without food for four hours.

Total cholesterol (TC) was determined enzymatically according to Siedel, J. et al, *J. Clin. Chem. Biochem.*, 19, p. 838 (1981). The quantitative analysis of the triglycerides (TG) was effected enzymatically by means of commercially available test kits [Boehringer/Mannheim] in an autoanalyzer [Hoffmann-La Roche/Basel] according to Wahlefeld, A. W. in Bergmeyer, H. U., "Methods of Enzymatic Analysis", Third edition, Vol. II, Verlag Chemie Press, Weinheim, 1878 (1974).

The lipid lowering effect is expressed by the percentage reduction of total cholesterol and the triglycerides with respect to the controls. The values for clofibrate are provided for purposes of comparison.

TABLE 4

Percentage reduction of the triglyceride (TG) and total cholesterol (TC) levels in the serum of rats following the oral application of the test substances.

| | % reduction | |
|---|---|---|
| | TG | TC |
| Clofibrate | $\bar{X} \pm S_x$ | $\bar{X} \pm S_x$ |
| Example Number | 29.2 ± 19.4 | 14.5 ± 12.0 |
| 4 | 53.3 ± 12.2 | 2.7 ± 9.2 |
| 5 | 40.6 ± 13.9 | 15.6 ± 14.4 |
| 7 | 46.3 ± 25.0 | 4.5 ± 20.2 |
| 8 | 52.1 ± 14.3 | 55.3 ± 16.5 |
| 11 | 38.4 ± 21.4 | 1.8 ± 14.2 |
| 13 | 42.2 ± 21.8 | 30.8 ± 22.2 |
| 15 | 57.5 ± 11.7 | 6.4 ± 14.6 |
| 16 | 69.0 ± 10.3 | 48.7 ± 9.2 |
| 17 | 41.9 ± 6.9 | 4.0 ± 17.7 |
| 20 | 50.6 ± 11.5 | 22.2 ± 7.4 |
| 21 | 46.0 ± 9.8 | 2.1 ± 24.4 |
| 23 | 48.9 ± 24.1 | 53.3 ± 15.3 |

TABLE 4-continued

Percentage reduction of the triglyceride (TG) and total cholesterol (TC) levels in the serum of rats following the oral application of the test substances.

| | % reduction | |
|---|---|---|
| | TG | TC |
| Clofibrate | $\bar{X} \pm S_x$ | $\bar{X} \pm S_x$ |
| Example Number | 29.2 ± 19.4 | 14.5 ± 12.0 |
| 25 | 51.9 ± 12.0 | 3.4 ± 12.1 |
| 26 | 44.1 ± 17.4 | 21.4 ± 10.1 |
| 27 | 52.1 ± 12.0 | 21.9 ± 15.4 |
| 28 | 50.5 ± 13.7 | 12.9 ± 33.9 |

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A compound comprising a p-oxybenzoic acid derivative of the formula (1)

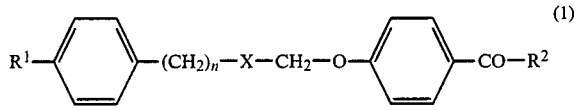

wherein
$R^1$ is hydrogen or straight or branched alkyl of one to four carbon atoms;
n is 1 or 2;
X is

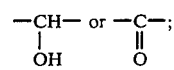

and
$R^2$ is —OH or —NHCH$_2$COOH; or a non-toxic, pharmaceutically acceptable salt thereof.

2. A compound of claim 1 wherein $R_1$ is hydrogen.

3. A compound of claim 1 wherein $R_1$ is methyl, ethyl, isopropyl or tertiary butyl.

4. A compound of claim 1 which is N-carboxymethyl-4-(2-hydroxy-4-phenylbutoxy)benzamide, or a non-toxic, pharmaceutically acceptable salt thereof.

5. A compound of claim 1 which is 4-[4-(4'-tert.-butylphenyl)-2-oxobutoxy]benzoic acid, or a non-toxic, pharmaceutically acceptable salt thereof.

6. A composition of matter comprising a hypolipemically effective amount of a compound or salt as claimed in claim 1, and a non-toxic, pharmaceutically acceptable carrier therefor.

7. A method of treating a mammal for hyperlipidemia which comprises administering to said mammal a hypolipemically effective amount of a compound or salt as claimed in claim 1.

8. A method of treating a mammal for hyperlipidemia which comprises adminstering to said mammal the composition as claimed in claim 6.

* * * * *

REEXAMINATION CERTIFICATE (2215th)
United States Patent
Grill et al.

[11] B1 4,582,857
[45] Certificate Issued Feb. 15, 1994

[54] P-OXYBENZOIC ACID DERIVATIVES PROCESSES FOR THEIR PRODUCTION AND THEIR USE AS DRUGS

[75] Inventors: Helmut Grill, Vaterstetten; Friedemann Reiter, Putzbrunn; Roland Löser, Feldafing; Michael Schliack, Munich; Klaus Seibel, Gräfelfing, all of Fed. Rep. of Germany

[73] Assignee: Klinge Pharma GmbH, Munich, Fed. Rep. of Germany

Reexamination Request:
No. 90/003,103, Jun. 22, 1993

Reexamination Certificate for:
Patent No.: 4,582,857
Issued: Apr. 15, 1986
Appl. No.: 632,650
Filed: Jul. 20, 1984

[30] Foreign Application Priority Data
Jul. 20, 1983 [DE] Fed. Rep. of Germany ....... 3326164

[51] Int. Cl.⁵ .................. A61K 31/195; C07C 103/29
[52] U.S. Cl. ..................................... 514/563; 514/568; 562/463; 562/444; 562/475
[58] Field of Search ............... 514/563, 568; 562/463, 562/444, 475

[56] References Cited
U.S. PATENT DOCUMENTS

| | | | |
|---|---|---|---|
| 3,586,713 | 6/1971 | Bure-Hoi et al. | 562/444 |
| 3,968,143 | 7/1976 | Schacht et al. | 424/317 |
| 4,067,892 | 1/1978 | Thorne et al. | 562/463 |
| 4,073,935 | 2/1978 | Grill et al. | 424/314 |
| 4,151,302 | 4/1979 | Gante et al. | 424/317 |
| 4,154,850 | 5/1979 | Morgan et al. | 424/317 |
| 4,189,594 | 2/1980 | Grill et al. | 424/317 |
| 4,277,497 | 7/1981 | Fromantin | 424/317 |

FOREIGN PATENT DOCUMENTS

0056172 7/1982 European Pat. Off. ............ 562/444

OTHER PUBLICATIONS

Morris et al "Organic Chemistry", pp. 1112–1113 (1966).
Fieser et al, "Reagents for Organic Synthesis", pp. 303–309 (1968).

*Primary Examiner*—James H. Reamer

[57] ABSTRACT

P-oxybenzoic acid derivatives of formula (1)

wherein
R¹ is hydrogen, or straight or branched alkyl of one to four carbon atoms;
n is 1 or 2;
X is

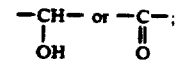

and
R² is —OH or —NHCH₂COOH; and non-toxic pharmaceutically acceptable salts thereof.

The compounds exhibit a hypolipemic effect. They may be prepared by methods known in themselves from the corresponding ester or acid halide compounds, wherein optionally the secondary alcohol group may be oxidized to a keto group.

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 6 and 7 are cancelled.

Claims 1-3 and 8 are determined to be patentable as amended.

Claims 4 and 5, dependent on an amended claim, are determined to be patentable.

New claims 9 to 13 are added and determined to be patentable.

1. A compound comprising a p-oxybenzoic acid derivative of the formula (1)

wherein
$R^1$ is hydrogen or straight or branched alkyl of one to four carbon atoms;
n is 1 or 2;
X is

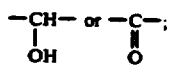

and
$R^2$ is —OH or —NHCH$_2$COOH; or a non-toxic, pharmaceutically acceptable salt thereof, *with the proviso that when $R^1$ is hydrogen, either X is*

*or $R^2$ is NHCH$_2$COOH;*

*or both X is*

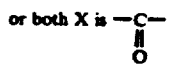

*and
$R^2$ is NHCH$_2$COOH.*

2. A compound of claim 1 wherein [R] $R^1$ is hydrogen.

3. A compound of claim 1 wherein [R$_1$] $R^1$ is methyl ethyl, isopropyl or tertiary butyl.

8. A method of treating a mammal for hyperlipidemia which comprises administering to said mammal the composition as claims in claim [6] 9.

9. *A composition of matter comprising a hypolipemically effective amount of a compound comprising a p-oxybenzoic acid derivative of the formula (1)*

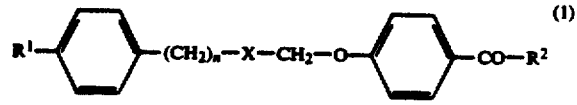

*wherein
$R^1$ is hydrogen or straight or branched alkyl of one to four carbon atoms;
n is 1 or 2;
X is*

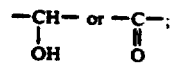

*and
$R^2$ is —OH or —NHCH$_2$COOH; or a non-toxic, pharmaceutically acceptable salt thereof, and a non-toxic, pharmaceutically acceptable carrier therefor.*

10. *A method of treating a mammal for hypolipidemia which comprises administering to said mammal a hypolipemically effective amount of a compound comprising a p-oxybenzoic acid derivative of the formula (1)*

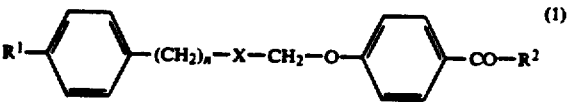

*wherein
$R^1$ is hydrogen or straight or branched alkyl of one to four carbon atoms;
n is 1 or 2;
X is*

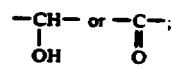

*and
$R^2$ is —OH or —NHCH$_2$COOH; or a non-toxic, pharmaceutically acceptable salt thereof.*

11. *A compound of claim 1, which is 4-[4-(4'-tert.butyl-phenyl)-2-hydroxybutoxy]benzoic acid, or a non-toxic, pharmaceutically acceptable salt thereof.*

12. *A composition of matter comprising a hypolipemically effective amount of a compound or salt as claimed in claim 1, and a non-toxic, pharmaceutically acceptable carrier therefor.*

13. *A method of treating a mammal for hyperlipidemia which comprises administering to said mammal the composition as claimed in claim 12.*

* * * * *